(12) United States Patent
Umeno

(10) Patent No.: US 9,714,928 B2
(45) Date of Patent: Jul. 25, 2017

(54) GAS-SENSOR CONTROL DEVICE

(71) Applicant: DENSO CORPORATION, Kariya, Aichi-pref. (JP)

(72) Inventor: Masafumi Umeno, Okazaki (JP)

(73) Assignee: DENSO CORPORATION, Kariya (JP)

( * ) Notice: Subject to any disclaimer, the term of this patent is extended or adjusted under 35 U.S.C. 154(b) by 125 days.

(21) Appl. No.: 14/662,645

(22) Filed: Mar. 19, 2015

(65) Prior Publication Data

US 2015/0268299 A1 Sep. 24, 2015

(30) Foreign Application Priority Data

Mar. 24, 2014 (JP) .................................. 2014-060401
Mar. 10, 2015 (JP) .................................. 2015-047508

(51) Int. Cl.
*G01N 33/00* (2006.01)
*G01N 27/406* (2006.01)
*F02B 77/08* (2006.01)

(52) U.S. Cl.
CPC ....... *G01N 33/007* (2013.01); *G01N 27/4065* (2013.01); *F02B 77/086* (2013.01)

(58) Field of Classification Search
CPC ............... F02B 77/086; F02D 35/0015; F02D 35/0046; F02D 35/0092; G01N 27/4065
See application file for complete search history.

(56) References Cited

U.S. PATENT DOCUMENTS

| 4,084,080 A * | 4/1978 | McMahan | A45D 44/00 122/459 |
| 4,868,710 A * | 9/1989 | Powell | A41D 13/008 2/244 |
| 6,724,160 B2 * | 4/2004 | Kaufman | H01J 27/14 313/37 |
| 2004/0153258 A1 | 8/2004 | Kurokawa et al. | |

FOREIGN PATENT DOCUMENTS

JP    2008-76191 A    4/2008

OTHER PUBLICATIONS

Mennie et al., "Sweep Frequency Singal Generator Design Techniques," Boonton Radio Corporation the Notebook, Spring, 1955, No. 5.*

* cited by examiner

*Primary Examiner* — Alexander Noguerola
(74) *Attorney, Agent, or Firm* — Posz Law Group, PLC

(57) ABSTRACT

A gas-sensor control device includes a sweep circuit, a return sweep circuit, and a control portion. The sweep circuit energizes a detection current to flow through an oxygen sensor to calculates an impedance of the oxygen sensor. The return sweep circuit energizes a neutralization current to flow through the oxygen sensor in a direction opposite to a direction of the detection current, so as to remove electricity from the oxygen sensor that is energized by the detection current. The control portion executes a detection of an off failure of the sweep circuit and the return sweep circuit, only (Continued)

based on a sensor voltage acquired in a time period where the neutralization current flows through the oxygen sensor, and a threshold.

7 Claims, 5 Drawing Sheets

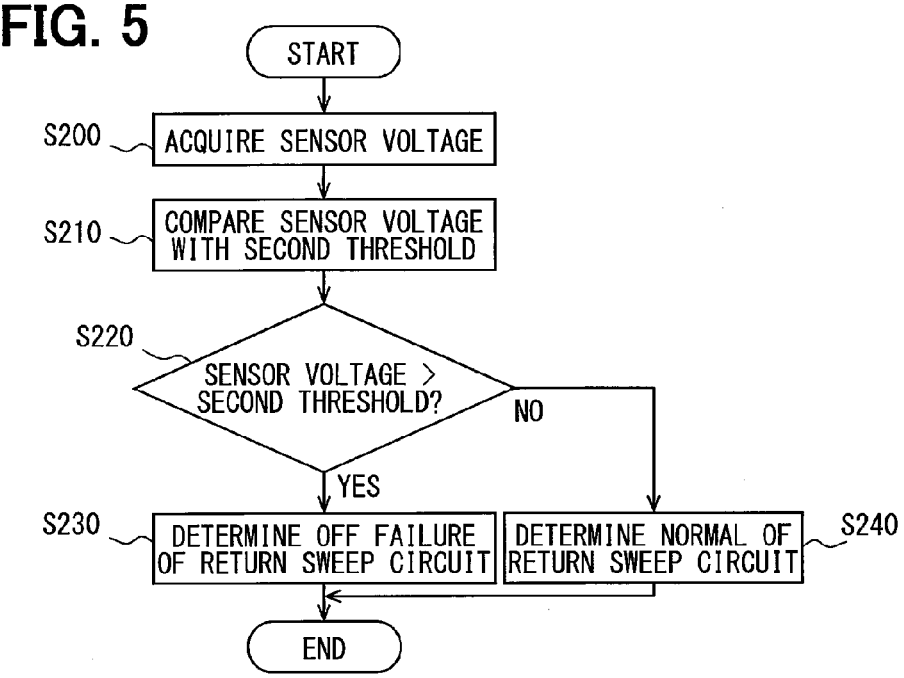
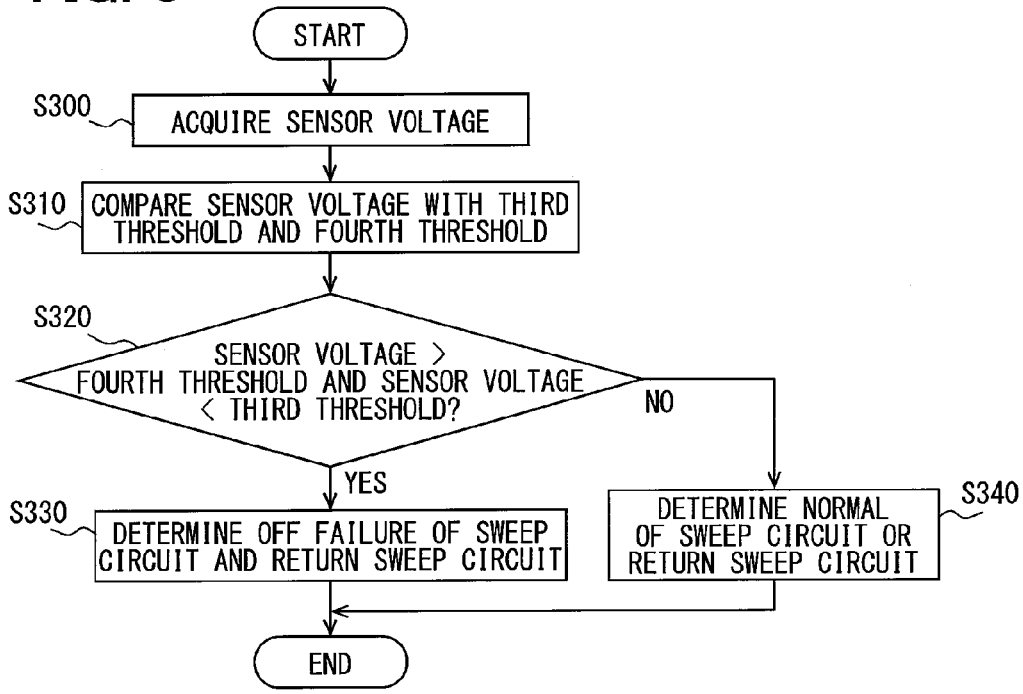

GAS-SENSOR CONTROL DEVICE

CROSS REFERENCE TO RELATED APPLICATION

This application is based on Japanese Patent Application No. 2014-60401 filed on Mar. 24, 2014 and Japanese Patent Application No. 2015-47508 filed on Mar. 10, 2015, the disclosures of which are incorporated herein by reference.

TECHNICAL FIELD

The present disclosure relates to a gas-sensor control device which acquires a temperature of a gas sensor by calculating an impedance of the gas sensor and executes a temperature control of the gas sensor based on the temperature of the gas sensor.

BACKGROUND

JP-2008-76191A discloses an off-failure diagnosis device of an oxygen sensor as an example of a gas-sensor control device.

The off-failure diagnosis device executes an off-failure diagnosis of the oxygen sensor generating an electromotive force according to a concentration of an oxygen in an exhaust gas. The off-failure diagnosis device includes an impedance detection circuit and an output-voltage detection circuit. The impedance detection circuit detects an impedance of the oxygen sensor in a case where a voltage is applied to the oxygen sensor. The output-voltage detection circuit detects an output voltage of the oxygen sensor. Further, the off-failure diagnosis device includes an off-failure determination portion. The off-failure determination portion compares a difference between the output voltage before the voltage is applied to the oxygen sensor and the output voltage after the voltage is applied to the oxygen sensor with a predetermined value, and determines an off failure of the oxygen sensor and an off failure of the impedance detection circuit.

When the impedance is detected, the off-failure diagnosis device determines whether the difference is greater than the predetermined value. When the off-failure diagnosis device determines that the difference is greater than the predetermined value, the off-failure diagnosis device compares the impedance with the predetermined value. When the impedance is greater than the predetermined value, the off-failure diagnosis device determines that the output voltage of the oxygen sensor is not generated. Therefore, the off-failure diagnosis device determines a second element has the off failure and the impedance detection circuit has the off failure.

However, since the off-failure diagnosis device uses the difference to determine the off failure of the second element, it is necessary to detect the output voltage before the voltage is applied to the oxygen sensor and the output voltage after the voltage is applied to the oxygen sensor. When the off-failure diagnosis device determines whether the first element turned on when being applied by the voltage has the off failure, the off-failure diagnosis device uses at least the output voltage before the voltage is applied to the oxygen sensor. The first element can be referred to as a sweep circuit. The second element can be referred to as a return sweep circuit.

When the off-failure diagnosis device determines whether the sweep circuit and the return sweep circuit have the off failure, it is necessary that the off-failure diagnosis device acquires the output voltage before the voltage is applied to the oxygen sensor and the output voltage after the voltage is applied to the oxygen sensor. In other words, the off-failure diagnosis device acquires the output voltage twice to determine the off failure. Therefore, in the off-failure diagnosis device, a control of a timing that the voltages are acquired becomes complicated.

SUMMARY

The present disclosure is made in view of the above matters, and it is an object of the present disclosure to provide a gas-sensor control device in which a timing control acquiring a voltage is simplified and an off failure of a sweep circuit and a return sweep circuit can be determined.

According to an aspect of the present disclosure, a gas-sensor control device is mounted to a vehicle.

The gas-sensor control device includes a sweep circuit, a return sweep circuit, an offset-voltage generating circuit, an acquiring circuit, and a control portion.

The sweep circuit energizes a detection current to flow through a gas sensor including an atmosphere-side electrode, an exhaust-side electrode, and a solid electrolyte portion, to calculate an impedance of the gas sensor. The electrolyte portion is interposed between the atmosphere-side electrode and the exhaust-side electrode.

The return sweep circuit energizes a neutralization current to flow through the gas sensor in a direction opposite to a direction of the detection current, to remove electricity from the gas sensor that is energized by the detection current.

When the neutralization current flows through the gas sensor, the offset-voltage generating circuit applies a voltage to the gas sensor such that a voltage of the atmosphere-side electrode is less than a voltage of the exhaust-side electrode.

The acquiring circuit acquires a voltage value between the atmosphere-side electrode and the exhaust-side electrode.

The control portion acquires a temperature of the gas sensor based on the impedance calculated by using the voltage value acquired by the acquiring circuit and a value of the detection current in a case where the detection current flows through the gas sensor. The control portion executes a temperature control of the gas sensor according to the temperature.

The control portion executes a detection of an off failure of the sweep circuit and the return sweep circuit, only based on the voltage value acquired by the acquiring circuit in a case where the neutralization current flows through the gas sensor, and a threshold.

The gas-sensor control device executes the detection of the off failure of the sweep circuit and the return sweep circuit, only based on the voltage value acquired by the acquiring circuit and the threshold. Therefore, the gas-sensor control device can detect the off failure without using a voltage value acquired by the acquiring circuit in a case where the detection current flows through the gas sensor. In other words, the gas-sensor control device can detect the off failure by acquiring the voltage value for only once. Thus, a control of a timing that the voltage value is acquired can be simplified. Further, the gas-sensor control device can simplify a software configuration for detecting the off failure.

BRIEF DESCRIPTION OF THE DRAWINGS

The above and other objects, features and advantages of the present disclosure will become more apparent from the following detailed description made with reference to the accompanying drawings. In the drawings:

FIG. 5 is a flowchart showing a determination processing of determining whether an off failure of a return sweep circuit of the control portion occurs, according to the embodiment;

FIG. 6 is a flowchart showing a determination processing of determining whether the off failure of the sweep circuit and the off failure of the return sweep circuit occur, according to the embodiment;

DETAILED DESCRIPTION

Figure 1:
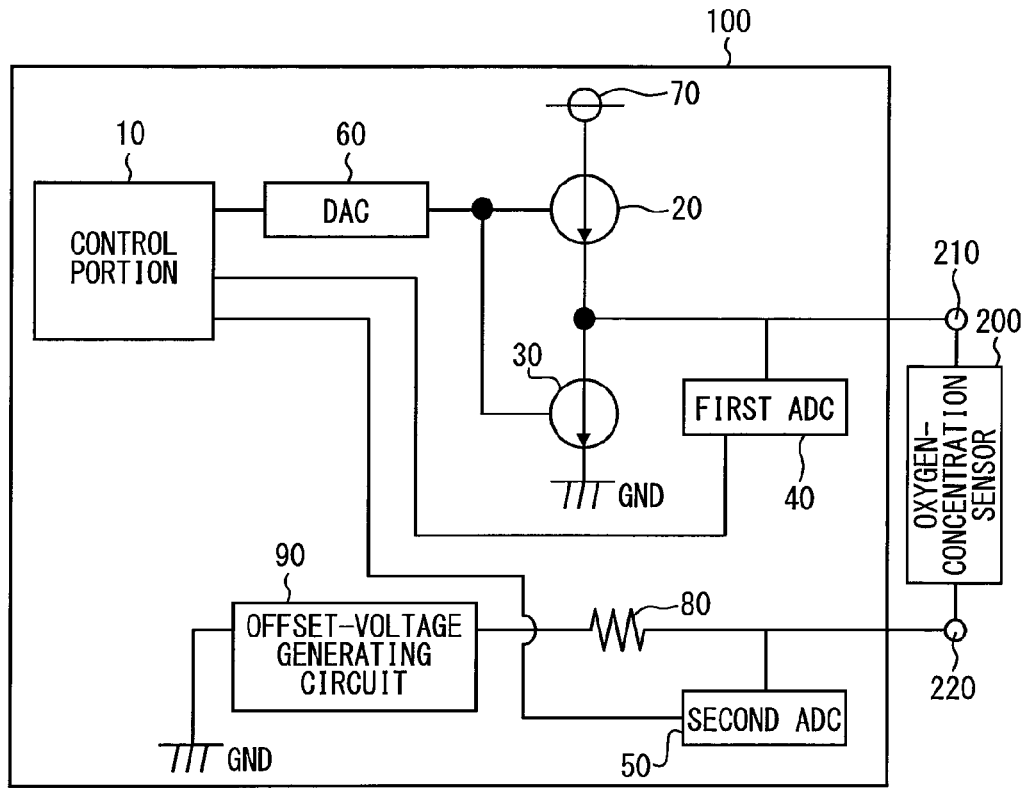
FIG. 1 is a block diagram showing an outline of an engine ECU according to an embodiment of the present disclosure.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

Hereafter, an embodiment of the present disclosure will be described referring to drawings. According to the embodiment, a gas-sensor control device is applied to an engine ECU 100.

The engine ECU 100 is mounted to a vehicle including an engine, and controls the engine. The engine ECU 100 is referred to as an ECU 100 hereafter. In addition, the ECU indicates an electronic control unit.

Figure 2:
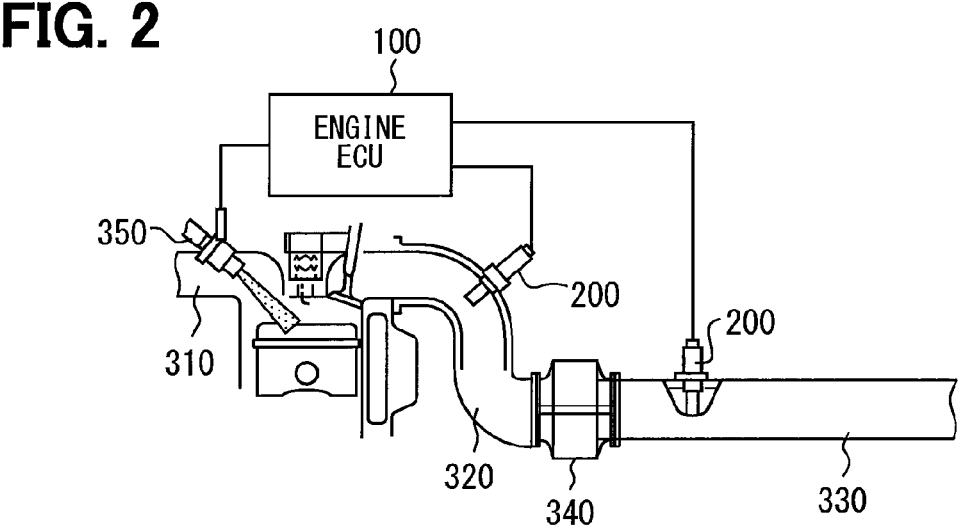
FIG. 2 is a diagram showing an outline of an engine including the engine ECU according to the embodiment.

As shown in FIG. 2, the ECU 100 is electrically connected with an injector 350 which is provided in an intake passage 310 of the engine, and oxygen-concentration sensors 200 which are provided in exhaust passages 320, 330 of the engine. According to the embodiment, one oxygen-concentration sensor 200 is provided in a first exhaust passage 320 upstream of a catalyst 340, and one oxygen-concentration sensor 200 is provided in a second exhaust passage 330 downstream of the catalyst 340. Hereafter, each oxygen-concentration sensor 200 is referred to as an oxygen sensor 200.

The oxygen sensor 200 is a gas sensor of the present disclosure. The oxygen sensor 200 includes a solid electrolyte portion, an atmosphere-side electrode 210, and an exhaust-side electrode 220. The solid electrolyte portion is interposed between the atmosphere-side electrode 210 and the exhaust-side electrode 220. In other words, in the oxygen sensor 200, a pair of electrodes which are the atmosphere-side electrode 210 and the exhaust-side electrode 220 are placed on surfaces of the solid electrolyte portion. In this case, the surfaces of the solid electrolyte portion are opposite to each other. The oxygen sensor 200 may be an oxygen sensor disclosed in JP-2008-76191A. A detail description of the oxygen sensor 200 will be omitted.

As shown in FIG. 1, the ECU 100 includes a control portion 10, a sweep circuit 20, a return sweep circuit 30, a first ADC 40, second ADC 50, a DAC 60, a power 70, a shunt resistance 80, and an offset-voltage generating circuit 90, which are elements of the gas-sensor control device. In addition, the ADC indicates an analog-to-digital converter, and the DAC indicates a digital-to-analog converter.

The control portion 10 includes a microcomputer having a CPU, a ROM, a RAM, a register, and an I/O. In addition, the CPU indicates a central processing unit, the ROM indicates a read only memory, the RAM indicates a random access memory, and the I/O indicates an input/output. Further, the control portion 10 is not limited to the above configuration. The control portion 10 can include a microcomputer and a customer specific IC.

In the control portion 10, the CPU uses a temporary storage function of the RAM of the register, and executes a signal processing according to a program previously stored in the ROM or a signal received through the I/O. The control portion 10 outputs a signal obtained by the signal processing through the I/O. The control portion 10 can execute various functions.

The control portion 10 loads an output of the oxygen sensor 200, calculates a mixture ratio of fuel to air in a combustion chamber, and controls a fuel injection quantity by using the injector 350. In this case, the mixture ratio is an NF value. The control portion 10 controls the fuel injection quantity by using the injector 350, based on a detection result of the oxygen sensor 200. The control portion 10 calculates an impedance of the oxygen sensor 200 by using a voltage value between the first ADC 40 and the second ADC 50 of when a detection current flows between the first ADC 40 and the second ADC 50 and a current value of the detection current. Specifically, the control portion 10 calculates a sensor voltage value based on the voltage value between the first ADC 40 and the second ADC 50. The sensor voltage value is a voltage value between the atmosphere-side electrode 210 and the exhaust-side electrode 220. The control portion 10 calculates the impedance of the oxygen sensor 200, by using the sensor voltage value and the current value of the detection current. A value of the impedance correlates to a temperature of the solid electrolyte portion. The control portion 10 acquires a sensor temperature that is the temperature of the solid electrolyte portion, by calculating the impedance of the oxygen sensor 200. The temperature of the solid electrolyte portion can be a temperature of the oxygen sensor 200.

The control portion 10 executes a temperature control of the oxygen sensor 200 according to the sensor temperature. When the sensor temperature is less than an activating temperature of the solid electrolyte portion, the control portion 10 controls the temperature of the solid electrolyte portion to become greater than or equal to the activating temperature by using a heater (not shown). The control portion 10 executes a detection of an off failure of the sweep circuit 20 and a detection of an off failure of the return sweep circuit 30. In the off failure, when the sweep circuit 20 or the return sweep circuit 30 is controlled to be turned on, the sweep circuit 20 or the return sweep circuit 30 is failed to be turned on, that is, the sweep circuit 20 or the return sweep circuit 30 is maintained to be turned off. The sweep circuit 20 and the return sweep circuit 30 are used to calculate the impedance of the oxygen sensor 200. According to the present embodiment, the detection of the off failure is referred to as an off-failure detection.

The sweep circuit 20 transmits the detection current to the oxygen sensor 200, so as to calculate the impedance of the oxygen sensor 200. The sweep circuit 20 is electrically connected with the DAC 60, the power 70, and the atmosphere-side electrode 210. The control portion 10 controls the sweep circuit 20 to energize the detection current or to deenergize the detection current. In other words, the control portion 10 indicates an energization of the detection current in the sweep circuit 20 through the DAC 60. The sweep circuit 20 applies a positive current to the oxygen sensor 200 by energizing the detection current.

The return sweep circuit 30 transmits a neutralization current to the oxygen sensor 200 in a direction opposite to a direction of the detection current, so as to remove electricity from the oxygen sensor 200 after the oxygen sensor 200 is energized by the detection current. When an electricity of the oxygen sensor 200 is not neutralized, an output voltage of the oxygen sensor 200 is continuously increased. Therefore, the oxygen sensor 200 cannot function as a sensor element. The return sweep circuit 30 is a circuit removing electricity from the oxygen sensor 200 after the oxygen sensor 200 is energized by the detection current.

The return sweep circuit 30 is electrically connected with the DAC 60, the sweep circuit 20, a ground (GND), and the atmosphere-side electrode 210. The control portion 10 controls the return sweep circuit 30 to energize the neutralization current or to deenergize the neutralization current. In other words, the control portion 10 indicates an energization of the neutralization current in the return sweep circuit 30 through the DAC 60.

The first ADC 40 and the second ADC 50 are circuits acquiring a voltage value between two electrodes of the oxygen sensor 200, and the first ADC 40 and the second ADC 50 correspond to an acquiring circuit. The first ADC 40 acquires a voltage value VAD1 of the atmosphere-side electrode 210, and outputs the voltage value VAD1 to the control portion 10. The second ADC 50 acquires a voltage value VAD2 of the exhaust-side electrode 220, and outputs the voltage value VAD2 to the control portion 10.

The DAC 60 is a member through which the control portion 10 controls a value of the detection current and a value of the neutralization current. The power 70 can use to supply power to an operation power of the ECU 100. The sweep circuit 20 and the return sweep circuit 30 are placed at positions between the power 70 and the ground.

The shunt resistance 80 is used for detecting current flowing through the oxygen sensor 200. The shunt resistance 80 is electrically connected with the exhaust-side electrode 220 and the offset-voltage generating circuit 90. When the neutralization current flows through the oxygen sensor 200, the offset-voltage generating circuit 90 applies a voltage to the oxygen sensor 200, such that an electrical potential of the atmosphere-side electrode 210 is less than an electrical potential of the exhaust-side electrode 220.

Figure 7:
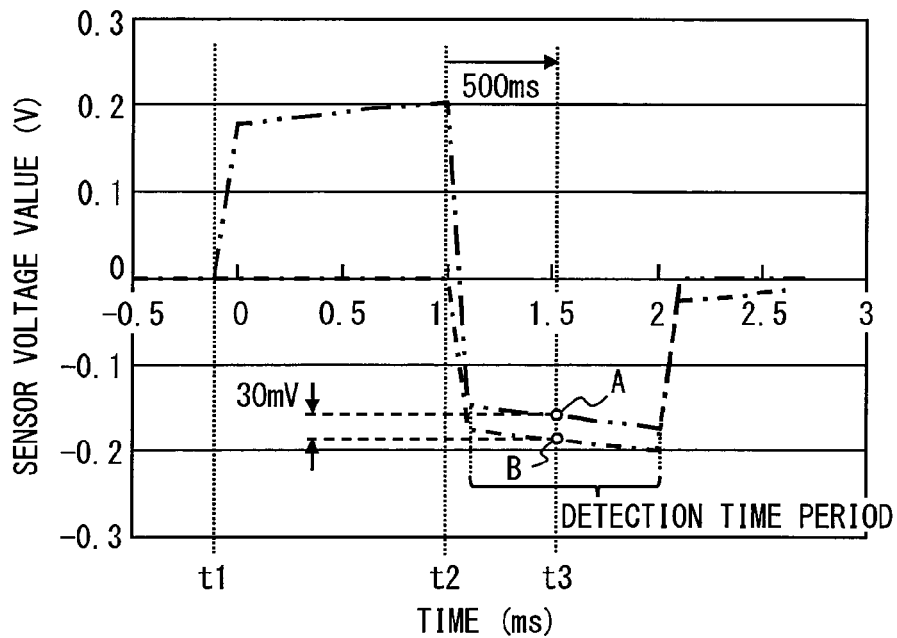
FIG. 7 is a time chart showing a relationship between a sensor voltage and time in the sweep circuit, according to the embodiment.
Figure 8:
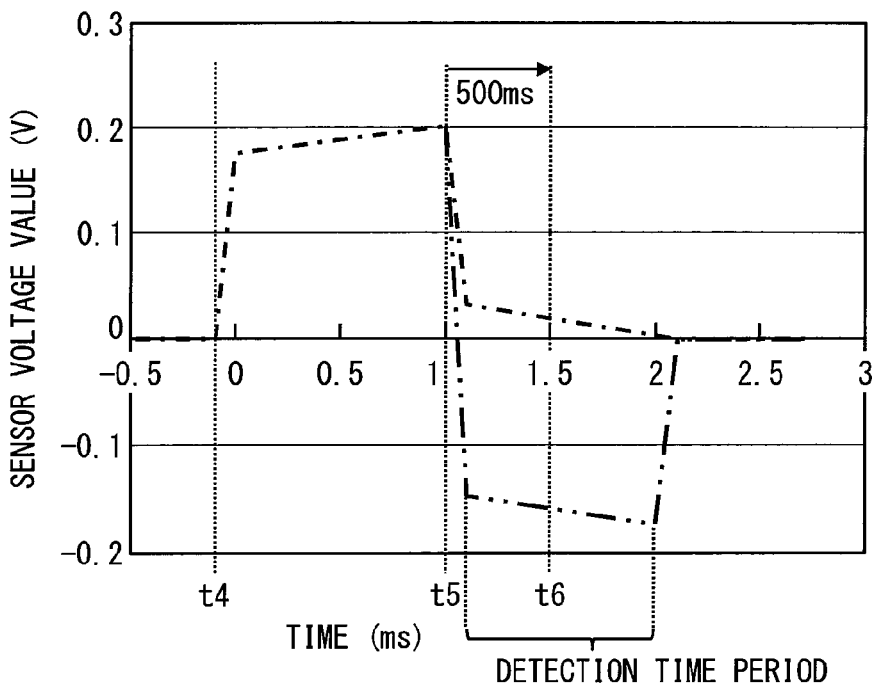
FIG. 8 is a time chart showing a relationship between a sensor voltage and time in the return sweep circuit, according to the embodiment.

Referring to FIGS. 3 to 8, a processing operation of the gas-sensor control device will be described. As shown in FIGS. 7 and 8, vertical axes indicate the sensor voltage, and horizontal axes indicate time. As shown in FIG. 7, a phantom line indicates a waveform of when the sweep circuit 20 and the return sweep circuit 30 are normal, and a center line indicates a waveform of when the sweep circuit 20 has the off failure and the return sweep circuit 30 is normal. According to the present embodiment, in the off failure of the sweep circuit 20, the sweep circuit 20 malfunctions in a case where the sweep circuit 20 is turned off. As shown in FIG. 8, a phantom line indicates a waveform of when the sweep circuit 20 and the return sweep circuit 30 are normal, and a center line indicates a waveform of when the sweep circuit 20 is normal and the return sweep circuit 30 has the off failure. According to the present embodiment, in the off failure of the return sweep circuit 30, the return sweep circuit 30 malfunctions in a case where the return sweep circuit 30 is turned off. As shown in FIG. 8, the phantom line has the same waveform as the center line before 1 ms. In addition, as shown in FIGS. 7 and 8, the sensor voltage is 0V before 0 ms.

Figure 3:
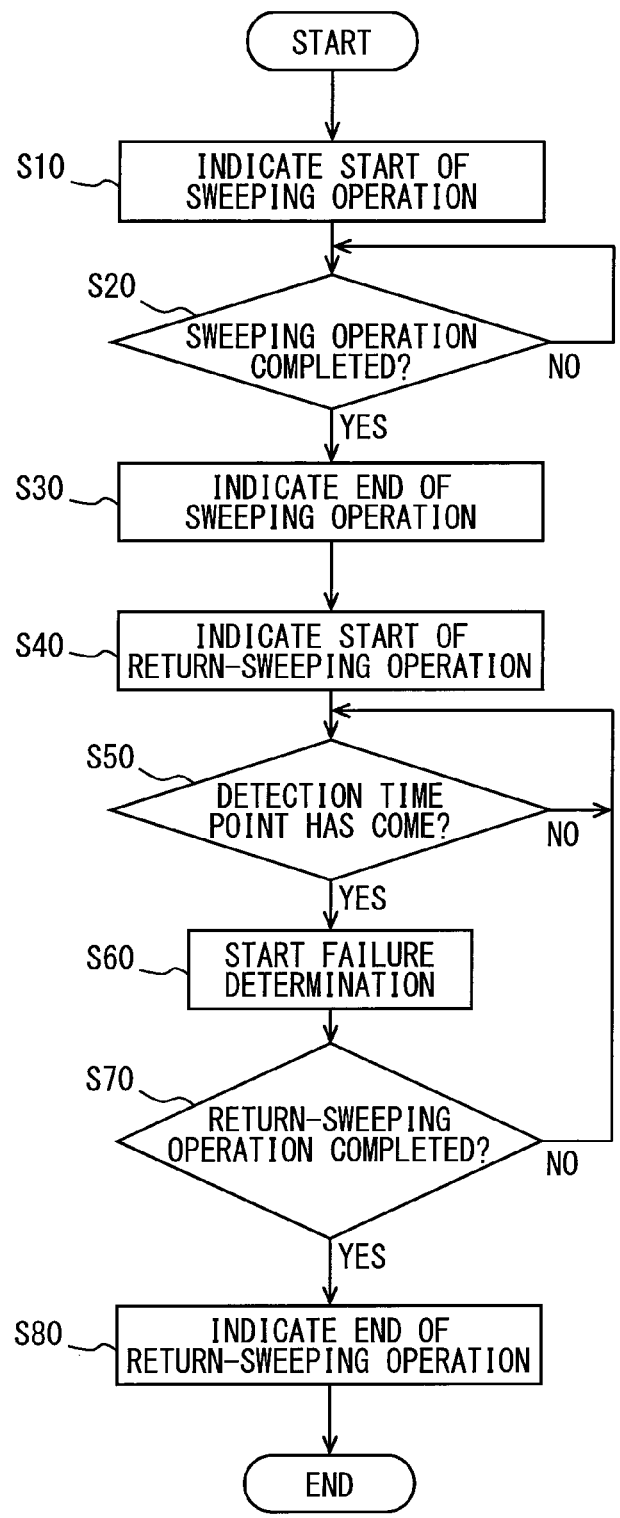
FIG. 3 is a flowchart showing an operation of a control portion according to the embodiment.

The control portion 10 executes an operation shown in FIG. 3. Specifically, the control portion 10 executes the operation at a timing different from a timing that the control portion 10 loads the output of the oxygen sensor 200. The timing that the control portion 10 loads the output of the oxygen sensor 200 is a timing that the control portion acquires an output value of the oxygen sensor 200 to control the fuel injection quantity by using the injector 350.

At S10, the control portion 10 indicates a start of a sweeping operation. The control portion 10 indicates the energization of the detection current to the sweep circuit 20. In this case, the control portion 10 does not indicate the energization of the neutralization current to the return sweep circuit 30. In other words, the control portion 10 turns on the sweep circuit 20 and turns off the return sweep circuit 30. Therefore, the detection current flows through the oxygen sensor 200.

As shown in FIG. 7, the control portion 10 indicates the energization of the detection current at a timing t1. As shown in FIG. 8, the control portion 10 indicates the energization of the detection current at a timing t4. When the sweep circuit 20 is normal, the sensor voltage is increased as the phantom lines shown in FIGS. 7 and 8 after the oxygen sensor 200 is energized by the detection current. Then, the sensor voltage is gradually increased until the energization of the detection current is completed at a timing t2 or t5. In this case, electric charge is accumulated in a capacity of the oxygen sensor 200 for 1 ms, for example. According to the present embodiment, the sensor voltage is increased to 0.2V. When the sweep circuit 20 has the off failure, the sweep circuit 20 shows a waveform different from that of the sweep circuit 20 of when the sweep circuit 20 is normal, as the center line shown in FIG. 7.

At S20, the control portion 10 determines whether the sweeping operation is completed. The control portion 10 determines whether a predetermined time period has elapsed from a time point that the control portion 10 indicates the start of the sweeping operation. When the control portion 10 determines that the predetermined time period has elapsed from the time point, the control portion 10 determines that the sweeping operation is completed and proceeds to S30. When the control portion 10 determines that the predetermined time period has not elapsed from the time point, the control portion 10 returns to S20 without terminating the sweeping operation. In other words, the control portion 10 keeps the energization of the detection current for the predetermined time period.

At S30, the control portion 10 indicates an end of the sweeping operation. At S40, the control portion 10 indicates a start of a return-sweeping operation. Specifically, the control portion 10 indicates a stop of the energization of the detection current to the sweep circuit 20, and indicates a start of the energization of the neutralization current to the return sweep circuit 30. In other words, the control portion 10 turns off the sweep circuit 20 and turns on the return sweep circuit 30. Therefore, in the oxygen sensor 200, the energization of the detection current is terminated, and the energization of the neutralization current is started.

As shown in FIG. 7, the control portion 10 indicates the energization of the detection current from the timing t1 to the timing t2, and indicates the energization of the neutralization current at the timing t2. As shown in FIG. 8, the control portion 10 indicates the energization of the detection current from the timing t4 to the timing t5, and indicates the energization of the neutralization current at the timing t5. The sensor voltage is immediately decreased after the energization of the neutralization current is started. Then, since the electric charge is leaked from the oxygen sensor 200, the sensor voltage is gradually decreased. When both the sweep circuit 20 and the return sweep circuit 30 are normal, the sensor voltage is gradually decreased until the energization of the neutralization current is completed. In this case, the electric charge is leaked from the oxygen sensor 200 for 2 ms, for example. Then, the sensor voltage is returned to an initial value that is 0V.

At S50, the control portion 10 determines whether a detection time point has come. The detection time point is a time point that the control portion 10 acquires the sensor voltage to execute the off-failure detection of the sweep circuit 20 and the return sweep circuit 30. The detection time point is established to be in a time period where the neutralization current flows through the oxygen sensor 200. Specifically, the detection time point is set to be in the time period where the neutralization current flows through the oxygen sensor 200, and in a time period where an output property indicating a frequency property of an impedance of the atmosphere-side electrode 210 and a frequency property of an impedance of the exhaust-side electrode 220. In this case, the time period is a detection time period as shown in FIGS. 7 and 8. In addition, as shown in FIGS. 7 and 8, the detection time period is 500 ms after a time point of the start of the energization of the neutralization current. When the control portion 10 determines that the detection time point has come, the control portion 10 proceeds to S60. When the control portion 10 determines that the detection time point has not come, the control portion 10 repeatedly executes a determination of S50.

At S60, the control portion 10 starts a failure determination. The control portion 10 executes the off-failure detection of the sweep circuit 20 and the return sweep circuit 30, based on the sensor voltage and a threshold in the time period where the neutralization current flows through the oxygen sensor 200. At S60, the control portion 10 executes processings shown in FIGS. 4 to 6. In addition, the control portion 10 may execute at least one of the processings shown in FIGS. 4 to 6.

At S70, the control portion 10 determines whether the return-sweeping operation is completed. The control portion 10 determines whether a predetermined time period has elapsed from a time point that the control portion 10 indicates the start of the return-sweeping operation. When the control portion 10 determines that the predetermined time period has elapsed from the time point, the control portion 10 determines that the return-sweeping operation is completed and proceeds to S80. When the control portion 10 determines that the predetermined time period has not elapsed from the time point, the control portion 10 returns to S50 without terminating the sweeping operation. In other words, the control portion 10 keeps the energization of the neutralization current for the predetermined time period.

At S80, the control portion 10 indicates an end of the return-sweeping operation. Specifically, the control portion 10 indicates a stop of the energization of the neutralization current to the return sweep circuit 30, without indicating the start of the energization of the detection current to the sweep circuit 20. In other words, the control portion 10 keeps turning off the sweep circuit 20 and turns off the return sweep circuit 30. Therefore, both the sweep circuit 20 and the return sweep circuit 30 are turned off.

Figure 4:
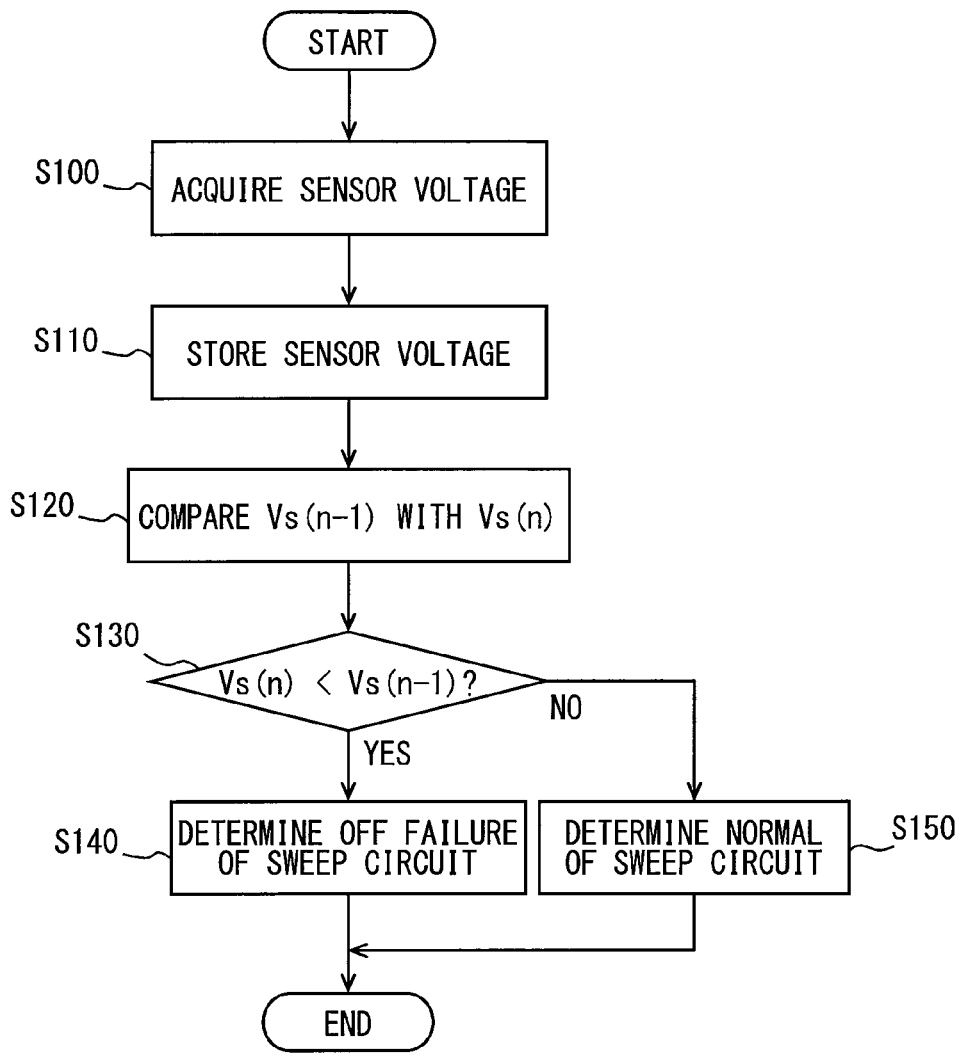
FIG. 4 is a flowchart showing a determination processing of determining whether an off failure of a sweep circuit of the control portion occurs, according to the embodiment.

Referring to FIG. 4, a first determination processing of determining whether the sweep circuit 20 has the off failure will be described. At S60, the control portion 10 executes the first determination processing as a flowchart shown in FIG. 4.

At S100, the control portion 10 acquires the sensor voltage. The control portion 10 acquires the sensor voltage based on an output value of the first ADC 40 and an output value of the second ADC 50.

At S110, the control portion 10 stores the sensor voltage. The control portion 10 stores the sensor voltage acquired at S100 in a storage portion such as the RAM. The control portion 10 updates the sensor voltage stored in the storage portion every time that the control portion 10 acquires the sensor voltage. In other words, the control portion 10 only stores one latest sensor voltage. The sensor voltage stored in the storage portion is a first threshold. That is, the control portion 10 uses the sensor voltage that is acquired and stored as the first threshold in a case where the neutralization current flows through the oxygen sensor 200 last time. According to the present embodiment, the sensor voltage stored in the storage portion is referred to as a previous value $Vs(n-1)$, and the sensor voltage acquired at S100 is referred to as a present value $Vs(n)$.

At S120, the control portion 10 compares the previous value $Vs(n-1)$ with the present value $Vs(n)$. In this case, the control portion 10 loads the sensor voltage from the storage portion. Then, the control portion 10 compares the sensor voltage $Vs(n-1)$ with the sensor voltage $Vs(n)$.

At S130, the control portion 10 determines whether the present value $Vs(n)$ is less than the previous value $Vs(n-1)$. When the control portion 10 determines that the present value $Vs(n)$ is less than the previous value $Vs(n-1)$, the control portion 10 proceeds to S140. When the control portion 10 determines that the present value $Vs(n)$ is greater than or equal to the previous value $Vs(n-1)$, the control portion 10 proceeds to S150. At S140, the control portion 10 determines that the sweep circuit 20 has the off failure. At S150, the control portion 10 determines that the sweep circuit 20 is normal. As the above description, the control portion 10 uses the sensor voltage as the first threshold to execute the off-failure detection of the sweep circuit 20.

As the center line shown in FIG. 7, when the sweep circuit 20 has the off failure, an operation of the sweep circuit 20 does not change until 1 ms. In this case, the sweep circuit 20 cannot energize the oxygen sensor 200 by the detection current. Therefore, the sensor voltage does not change.

When the return sweep circuit 30 is turned on at the timing t2, the sensor voltage is immediately decreased. The sensor voltage of when the sweep circuit 20 has the off failure is less than the sensor voltage of when the sweep circuit 20 is normal, and a difference therebetween is equal to the electric charge accumulated in the oxygen sensor 200. When the present value $Vs(n)$ is less than the previous value $Vs(n-1)$, the control portion 10 can determine that the sweep circuit 20 has the off failure. For example, as shown in FIG. 7, the previous value is a value of a point A, and the present value is a value of a point B. In this case, the control portion 10 determines that the sweep circuit 20 has the off failure. The control portion 10 can detect the off failure of the sweep circuit 20 only based on the sensor voltage acquired at S100 and the first threshold. In other words, the control portion 10 can detect the off failure of the sweep circuit 20 by using an effect that is generated by the electric charge accumulated in the capacity of the oxygen sensor 200 and is applied to the sensor voltage of when the neutralization current is energized to flow through the oxygen sensor 200. Alternatively, the control portion 10 can detect a timing that the off failure of the sweep circuit 20 is generated.

According to the present disclosure, the control portion 10 may determine that the sweep circuit 20 has the off failure in a condition that the present value Vs(n) is less than the previous value Vs(n−1) and the difference between the present value Vs(n) and the previous value Vs(n−1) is greater than a predetermined value. In this case, the difference is value that the present value Vs(n) is subtracted from the previous value Vs(n−1).

A differential value between the sensor voltage of when the sweep circuit 20 is normal and the sensor voltage of when the sweep circuit 20 has the off failure is established by the capacity of the oxygen sensor 200. As shown in FIG. 7, the differential value is 30 mV. The predetermined value is set based on the differential value established by the capacity of the oxygen sensor 200. The predetermined value can be set by considering a detection accuracy of the sensor voltage and a variation quantity of the sensor voltage generated since the detection current is energized to flow through the oxygen sensor 200. The detection accuracy of the sensor voltage includes a converting accuracy of the first ADC 40 or a converting accuracy of the second ADC 50. When the differential value is 30 mV, the predetermined value is set to be 20 mV by considering the detection accuracy and the variation quantity. In this case, when the difference is greater than 20 mV, the control portion 10 determines that the sweep circuit 20 has the off failure.

According to the present disclosure, the control portion 10 can detect the off failure of the sweep circuit 20, based on the sensor voltage acquired at S100, the first threshold, and the predetermined value. Further, when the control portion 10 determines whether the sweep circuit 20 has the off failure, an erroneous determination generated due to an error of the sensor voltage can be suppressed.

At S110, the control portion 10 may store plural sensor voltages, that is, the control portion 10 may store past sensor voltages and the latest sensor voltage. In this case, at S120, the control portion 10 may calculate an average value of the plural sensor voltages and compare the sensor voltage acquired at S100 with the average value. In other words, the control portion 10 uses the average value as the previous value. Further, the average value is the first threshold. Thus, the control portion 10 uses the first threshold that is the average of the plural sensor voltages to execute the off-failure detection of the sweep circuit 20. Therefore, according to the present disclosure, the control portion 10 can detect the off failure of the sweep circuit 20, only based on the sensor voltage acquired at S100 and the first threshold. Further, when the control portion 10 determines whether the sweep circuit 20 has the off failure by using the average value as the first threshold, the erroneous determination generated due to the error of the sensor voltage can be suppressed.

Referring to FIG. 5, a second determination processing of determining whether the return sweep circuit 30 has the off failure will be described. At S60, the control portion 10 executes the second determination processing as a flowchart shown in FIG. 5.

At S200, the control portion 10 acquires the sensor voltage. Since a processing of S200 is as the same as a processing of S100, a description of S200 is omitted.

At S210, the control portion 10 compares the sensor voltage with a second threshold. The control portion 10 compares the sensor voltage acquired at S200 with the second threshold. The second threshold is a positive voltage value. Further, the second threshold is previously established and is stored in the storage portion.

At S220, the control portion 10 determines whether the sensor voltage is greater than the second threshold. When the control portion 10 determines that the sensor voltage is greater than the second threshold, the control portion 10 proceeds to S230. When the control portion 10 determines that the sensor voltage is less than or equal to the second threshold, the control portion 10 proceeds to S240.

At S230, the control portion 10 determines that the return sweep circuit 30 has the off failure. At S240, the control portion 10 determines that the return sweep circuit 30 is normal. As the above description, the control portion 10 uses the second threshold that is a positive voltage value to execute the off-failure detection of the return sweep circuit 30. The second threshold is a voltage value that cannot be acquired from the return sweep circuit 30 which is normal. According to the present embodiment, the second threshold is 10 mV.

As shown in FIG. 8, when the return sweep circuit 30 is normal, the sensor voltage becomes a negative voltage value and then becomes close to 0V, after the timing t5 that the energization of the neutralization current is indicated by the control portion 10. When the off failure of the return sweep circuit 30 is generated, the sensor voltage is maintained to be greater than or equal to 0V and gradually approaches to 0V.

When the return sweep circuit 30 has the off failure, the sensor voltage is maintained to be greater than or equal to 0V by the electric charge accumulated in the capacity of the oxygen sensor 200 according to the energization of the detection current. In other words, when the return sweep circuit 30 has the off failure, the sensor voltage does not become a negative voltage.

When the sensor voltage is greater than the second threshold, the control portion 10 can determine that the return sweep circuit 30 has the off failure. The control portion 10 can detect the off failure of the return sweep circuit 30, only based on the sensor voltage acquired at S200 and the second threshold.

In addition, the second threshold may be equal to 0V. However, according to the present disclosure, considering a detection accuracy of the sensor voltage, it is preferable that the second threshold is greater than 0V. Since the second threshold uses the positive voltage value, when the control portion 10 detects whether the return sweep circuit 30 has the off failure, an erroneous determination due to an error of the sensor voltage detected in the detection time point can be suppressed.

Referring to FIG. 6, a third determination processing of determining whether both the sweep circuit 20 and the return sweep circuit 30 have the off failure will be described. At S60, the control portion 10 executes the third determination processing as a flowchart shown in FIG. 6.

At S300, the control portion 10 acquires the sensor voltage. Since a processing of S300 is as the same as the processing of S100, a description of S300 is omitted.

At S310, the control portion 10 compares the sensor voltage with a third threshold and a fourth threshold voltage. The control portion 10 compares the sensor voltage acquired at S300 with the third threshold that is a positive voltage value and the fourth threshold that is a negative voltage value. The third threshold and the fourth threshold are previously established and are stored in the storage portion.

At S320, the control portion 10 determines whether the sensor voltage is between the third threshold and the fourth threshold. In other words, the control portion 10 determines whether the sensor voltage is greater than the fourth threshold and is less than the third threshold. When the control portion 10 determines that the sensor voltage is between the third threshold and the fourth threshold, the control portion 10 proceeds to S330. When the control portion 10 determines that the sensor voltage is not between the third threshold and the fourth threshold, the control portion 10 proceeds to S340.

At S330, the control portion 10 determines that both the sweep circuit 20 and the return sweep circuit 30 have the off failure. In other word, the control portion 10 determines that the sweep circuit 20 and the return sweep circuit 30 have the off failure at the same time. At S340, the control portion 10 determines that the sweep circuit 20 or the return sweep circuit 30 is normal. As the above description, the control portion 10 uses the third threshold and the fourth threshold to execute the off-failure detection of the sweep circuit 20 and the return sweep circuit 30.

Both the third threshold and the fourth threshold are voltage values that cannot be acquired in a case where both the sweep circuit 20 and the return sweep circuit 30 are normal. According to the present embodiment, the third threshold can be established to positive 10 mV, and the fourth threshold can be established to negative 10 mV.

When both the sweep circuit 20 and the return sweep circuit 30 have the off failure, the sensor voltage becomes 0V. Further, when the control portion 10 determines that the sensor voltage is between the third threshold and the fourth threshold, the control portion 10 can determine that both the sweep circuit 20 and the return sweep circuit 30 have the off failure. As the above description, the control portion 10 can execute the off-failure detection the sweep circuit 20 and the return sweep circuit 30, based on the sensor voltage acquired at S300, the third threshold, and the fourth threshold.

When both the sweep circuit 20 and the return sweep circuit 30 have the off failure, the sensor voltage becomes 0V. The control portion 10 may execute the off-failure detection of the sweep circuit 20 and the return sweep circuit 30 by determining whether the sensor voltage acquired at S300 is equal to 0V. In other words, when the sensor voltage is equal to 0V, the control portion 10 may determine that both the sweep circuit 20 and the return sweep circuit 30 have the off failure. However, the sensor voltage acquired at S300 may have an error.

According to the present disclosure, it is preferable that the off failure is detected by using the third threshold and the fourth threshold. Since the third threshold and the fourth threshold are used, when the control portion 10 determines whether the off failure is generated, the erroneous determination due to the error of the sensor voltage can be suppressed.

As the above description, the gas-sensor control device can detect the off failure only based on the sensor voltage acquired in a case where the neutralization current is energized to flow through the oxygen sensor 200. That is, the gas-sensor control device detects the off failure without using the sensor voltage acquired in a case where the detection current is energized to flow through the oxygen sensor 200. In other words, the gas-sensor control device can detect the off failure by acquiring the sensor voltage for once. Therefore, the gas-sensor control device can simplify a control of a timing that the sensor voltage is acquired. Further, the gas-sensor control device can simplify a software configuration for detecting the off failure.

The off failure can be detected by using a voltage float. In the voltage float, as shown in FIG. 8(B) of JP-2008-76191A, a detected voltage is increased after being applied by a voltage in a case where an impedance detection circuit has an off failure. A level of the voltage float varies according to a magnitude of a self-discharge of the gas sensor. The self-discharge of the gas sensor depends on a temperature of the gas sensor and a variation of elements of the gas sensor. When the voltage float is used to determine whether the off failure is generated, the off failure cannot be surely detected.

However, the gas-sensor control device can detect the off failure, only based on the sensor voltage acquired in a case where the neutralization current is energized to flow through the oxygen sensor 200. Therefore, the gas-sensor control device can detect the off failure of the sweep circuit 20 of the off failure of the return sweep circuit 30, without respect to an individual difference of the oxygen sensor 200.

According to the present embodiment, in a current control, the detection current and the neutralization current are energized to flow through the oxygen sensor 200. However, the present disclosure is not limited to the above configuration. The present disclosure can be applied to a voltage control in which the detection current and the neutralization current are energized to flow through the oxygen sensor 200.

The present disclosure is not limited to the embodiments mentioned above, and can be applied to various embodiments within the spirit and scope of the present disclosure.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A gas-sensor control device mounted to a vehicle comprising:
a sweep circuit energizing a detection current to flow through a gas sensor including an atmosphere-side electrode, an exhaust-side electrode, and a solid electrolyte portion, the solid electrolyte portion being interposed between the atmosphere-side electrode and the exhaust-side electrode;
a return sweep circuit energizing a neutralization current to flow through the gas sensor in a direction opposite to a direction of the detection current, to discharge accumulated electric charge from the gas sensor that is energized by the detection current;
an offset-voltage generating circuit applying a voltage to the gas sensor such that a voltage of the atmosphere-side electrode is less than a voltage of the exhaust-side electrode, when the neutralization current flows through the gas sensor;
an acquiring circuit acquiring a voltage value between the atmosphere-side electrode and the exhaust-side electrode;
a control portion acquiring a temperature of the gas sensor based on an impedance of the gas sensor calculated by using the voltage value acquired by the acquiring circuit and a value of the detection current in a case where the detection current flows through the gas sensor, the control portion executing a temperature control of the gas sensor according to the temperature, wherein the control portion executes a detection of an off failure of the sweep circuit and the return sweep circuit, only based on the voltage value acquired by the acquiring circuit in a time period where the neutralization current flows through the gas sensor, and a threshold, and in the off failure, the sweep circuit or the return sweep circuit is maintained to be turned off while the sweep circuit or the return sweep circuit is controlled to be turned on.

2. The gas-sensor control device according to claim 1, wherein the control portion stores the voltage value acquired by the acquiring circuit in the time period as the threshold, the control portion executes the detection of the off failure of the sweep circuit by using the voltage value as a first threshold, and when a present voltage value acquired by the acquiring circuit is less than the first threshold, the control portion determines that the sweep circuit has the off failure.

3. The gas-sensor control device according to claim 2, wherein the control portion uses the voltage value acquired and stored as the first threshold in the time period where the neutralization current flows through the gas sensor last time, to execute the detection of the off failure of the sweep circuit.

4. The gas-sensor control device according to claim 2, wherein the control portion stores plural voltage values acquired by the acquiring circuit in the time period, and the control portion executes the detection of the off failure by using an average of the voltage values as the first value.

5. The gas-sensor control device according to claim 2, wherein when the voltage value acquired by the acquiring circuit is less than the first threshold and a difference between the first threshold and the voltage value is greater than a predetermined value, the control portion determines that the sweep circuit has the off failure.

6. The gas-sensor control device according to claim 1, wherein the control portion executes the detection of the off failure of the return sweep circuit by using a second threshold that is a positive voltage value as the threshold, and when the voltage value acquired by the acquiring circuit is greater than the second threshold, the control portion determines that the return sweep circuit has the off failure.

7. The gas-sensor control device according to claim 1, wherein the control portion executes the detection of the off failure of the sweep circuit and the return sweep circuit by using a third threshold that is a positive voltage value and a fourth threshold that is a negative voltage value, and when the voltage value is less than the third threshold and is greater than the fourth threshold, the control portion determines that both the sweep circuit and the return sweep circuit have the off failure.

* * * * *